United States Patent [19]

Gonser

[11] Patent Number: 4,608,622
[45] Date of Patent: Aug. 26, 1986

[54] MULTI-FUNCTION LIGHT SOURCE

[75] Inventor: Donald I. Gonser, York, Pa.

[73] Assignee: Dentsply Research & Development Corp., Milford, Del.

[21] Appl. No.: 681,324

[22] Filed: Dec. 14, 1984

Related U.S. Application Data

[63] Continuation-in-part of Ser. No. 566,235, Dec. 28, 1983, Pat. No. 4,516,195.

[51] Int. Cl.[4] .............................................. F21V 7/04
[52] U.S. Cl. .................................... 362/32; 362/281; 362/293; 362/804
[58] Field of Search ................. 362/32, 268, 277, 281, 362/293, 297, 310, 323, 346, 804, 255, 269, 283

[56] References Cited

U.S. PATENT DOCUMENTS

| | | | |
|---|---|---|---|
| 3,446,952 | 5/1969 | Sitter et al. | 362/32 |
| 3,832,539 | 8/1974 | Oram | 362/293 |
| 3,842,254 | 10/1974 | Dianetti | 362/282 |
| 4,009,382 | 2/1977 | Nath | 362/32 |
| 4,196,460 | 4/1980 | Schreckendgust | 362/231 |
| 4,356,534 | 10/1982 | Hattori | 362/32 |
| 4,400,765 | 8/1983 | Kochem | 362/277 |
| 4,450,139 | 5/1984 | Bussiere et al. | 422/186.3 |

FOREIGN PATENT DOCUMENTS

| | | | |
|---|---|---|---|
| 2604921 | 8/1977 | Fed. Rep. of Germany | |
| 536887 | 5/1941 | United Kingdom | 362/32 |

Primary Examiner—Craig R. Feinberg
Assistant Examiner—David A. Okonsky
Attorney, Agent, or Firm—Woodcock Washburn Kurtz Mackiewicz & Norris

[57] ABSTRACT

A multi-function dental operating light source comprises a plurality of optical filters and reflectors mounted upon a turntable at spaced locations around the periphery thereof, the turntable being rotatable to different predetermined positions relative to a collimated light source to produce selectable different modes of light delivery. The optical filters are adapted respectively to produce light beams for shade-matching, no-cure to prevent polymerization of light-curable resins when exposed to said light for observation purposes, a photocuring light beam, and beams for oral illumination and transillumination. The photocuring light is preferably developed by condensing the collimated light through a light-condensing cone or through an optical condensing system, the condensed light being delivered either directly from the condenser output or through a light pipe arrangement.

17 Claims, 10 Drawing Figures

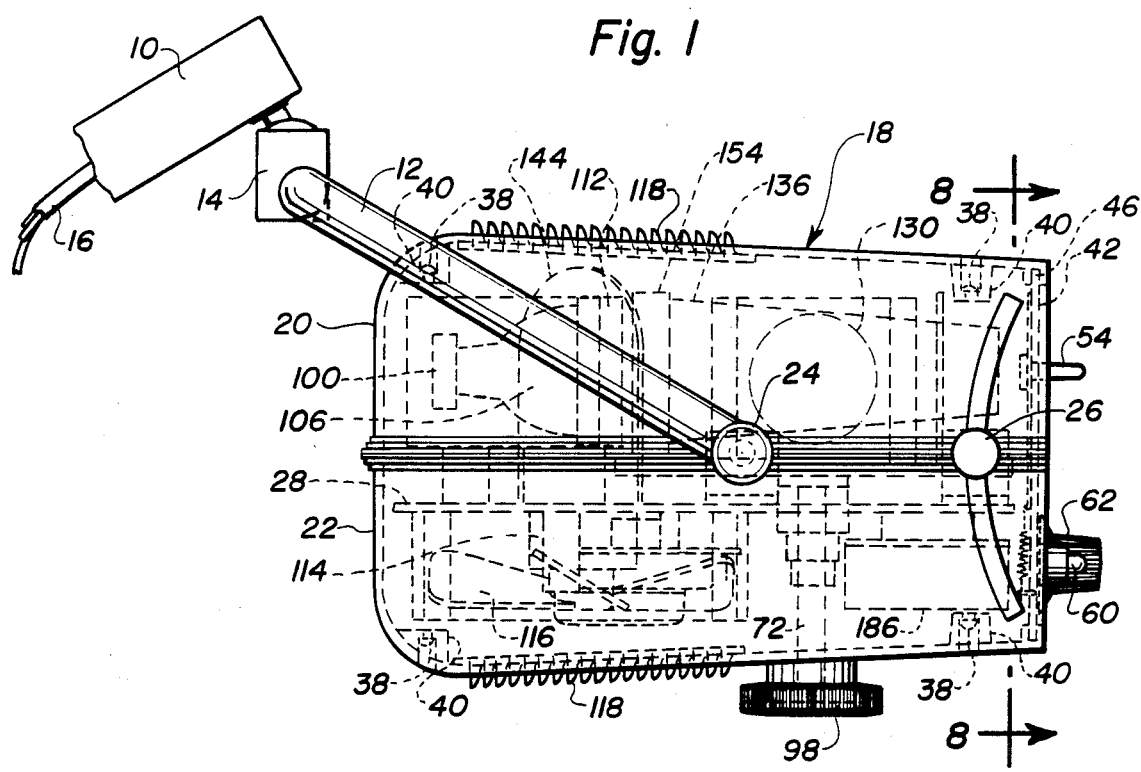
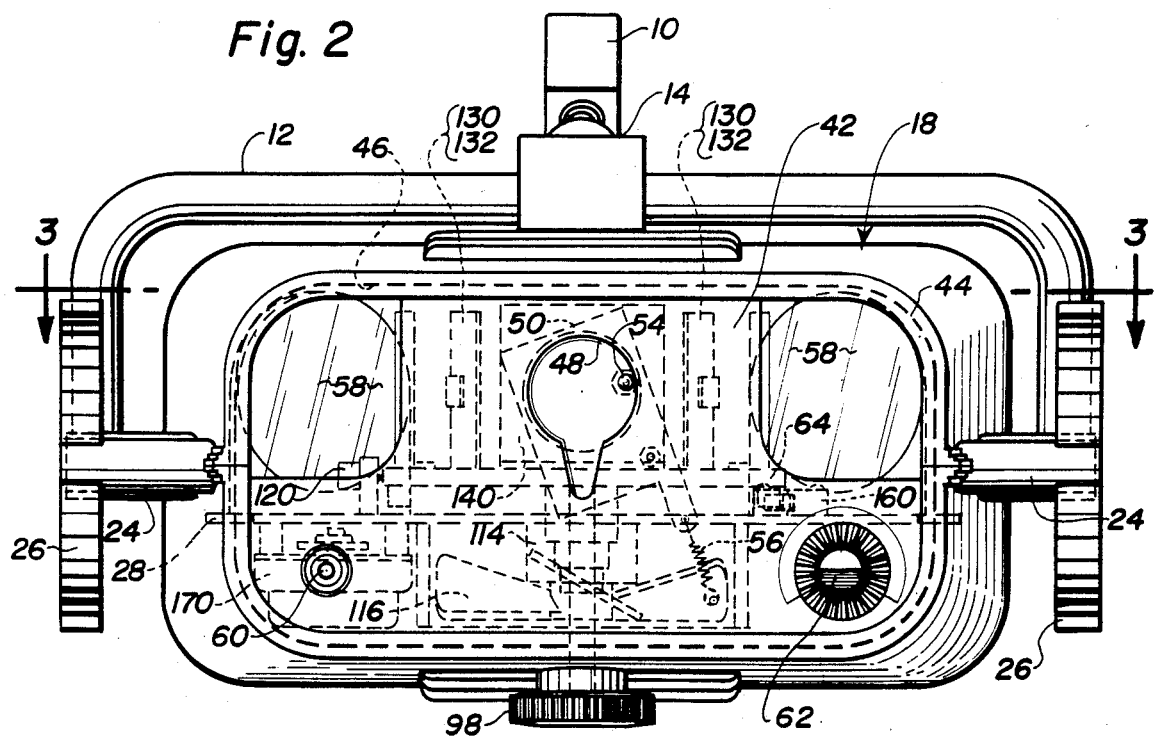

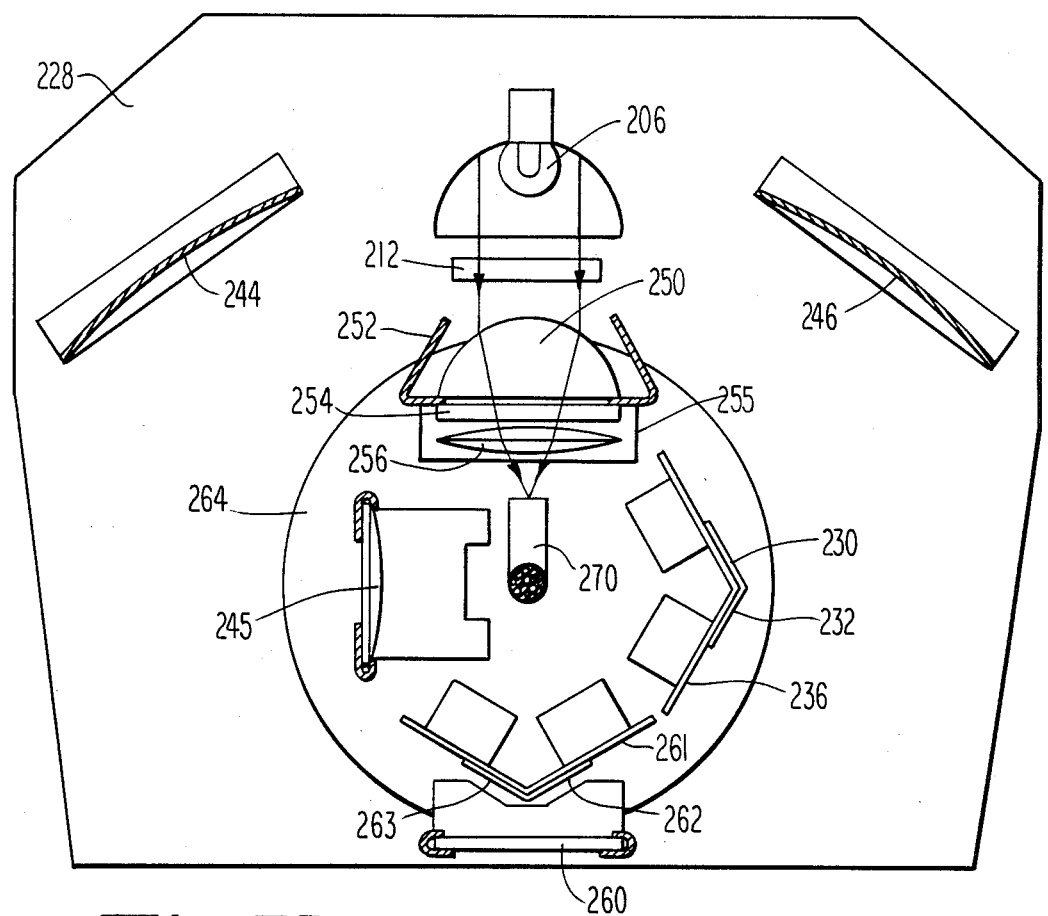
_Fig. 7B_
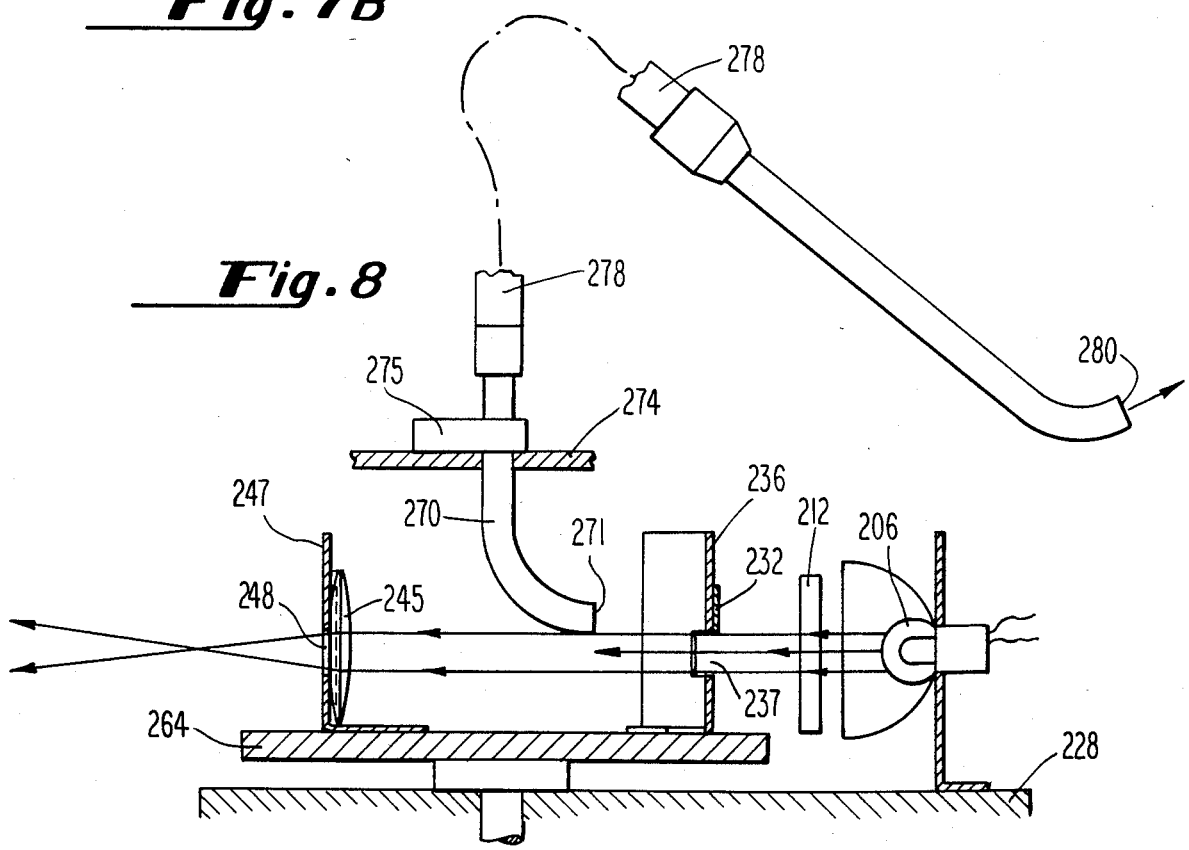
_Fig. 8_

MULTI-FUNCTION LIGHT SOURCE

REFERENCE TO RELATED APPLICATION

This is a Continuation-In-Part of my co-pending application Ser. No. 566,235, filed Dec. 28, 1983 and now U.S. Pat. No. 4,516,195, assigned to the same assignee.

BACKGROUND OF THE INVENTION

In modern dental practice, different types of illumination and photocuring functions are required and, at present, these, in general, are supplied respectively by individual different lamps packaged as separate light sources, thus requiring a number of individual pieces of equipment for use in a dental operatory. Also, at present, high rents necessitate maintaining operatory rooms in relatively small economical sizes, whereby the smaller, simpler, and less space-consuming equipment is, the better it can be accommodated comfortably in present day operatories. The present invention is directed to such minimizing of required illumination equipment as well as rendering the same more efficient and of improved quality.

For many years, it has been customary for dentists to select operatories facing north wherever possible in order to obtain natural daylight as close as possible to pure white light, i.e., the absence of color hue. Such efforts are frustrated on cloudy or rainy days and the time of the year, however, whereby one has to resort to using artificial light from lamp sources upon which attempts have been made to modify the same to at least approach pure white light at an acceptable color temperature.

Dentistry presently requires illumination of as nearly as possible pure white light to be directed at dental targets for viewing the same such as the interior of an oral cavity; similar somewhat intensified white light illumination suitable for shade matching of artificial teeth with natural teeth; photocure light power of a type to effect curing of light-curable resins or plastics used for dental restorations of various kinds and similar purposes; and illumination of dental targets of a type which permits viewing the same without effecting premature polymerization of visible light-curable resins or plastics, such as those used for dental restorations of various kinds and especially while forming and shaping fillings and similar restorations of plastic material prior to curing the same. As indicated above, lights or lamps to produce standard illumination now are available only as individual units. As far as is known, a no-cure type of illumination is not available to date.

In the prior art of lighting and illumination in general, attempts have been made to utilize a single light source to produce, for example, different colors for entertainment and stage use. Typical examples of this type of illumination are illustrated in prior U.S. Pat. Nos. 2,606,477 to Leslie et al, dated Aug. 12, 1952 and 3,179,791 to Mole, dated Apr. 20, 1965. As a slight modification of the principles illustrated in the foregoing patents, prior U.S. Pat. No. 2,699,536 to Roth et al, dated Jan. 11, 1955 discloses a headlamp arrangement on certain vehicles for signaling purposes and in which the light source remains fixed and movable lenses cause the projections of a spiral pattern of beams.

There also has been prior activity in reflecting beams from a light source in a manner to intensify beams therefrom by reflection to and from curved reflectors for ultimate direction through an output window or lens, one example being the subject matter of prior U.S. Pat. No. 3,202,811 to Hall, Jr., dated Aug. 24, 1965.

Unlike the operation and construction of these cited prior art patents, the present invention utilizes a single lamp as a light source and by means of a series of light modifying optical filters and related elements, coupled with variable control of voltage to the filament of the light source, at least most if not all of the various types of dental applications for illumination and photocuring set forth above can be produced by relatively simple structures of a compact nature, details of which are set forth below.

The present invention is the result of expanding and increasing the versatility and convenience of the inventions in Applicant's prior U.S. Pat. No. 4,385,344, dated May 24, 1983, U.S. application Ser. No. 492,286, filed May 6, 1983 still pending, and parent application Ser. No. 566,235 now U.S. Pat. No. 4,516,195, filed Dec. 28, 1983.

SUMMARY OF THE INVENTION

Among basic objects of the present invention, it is a major objective to provide a multi-function light source, for dental and other uses, which employs a single light source and a rotatable turntable having mounted thereon a limited number of light beam modifiers of said light source, for selective positioning relative to said light source, whereby a plurality of required dental illumination needs and photocuring functions are supplied by a single instrument.

Ancillary to the foregoing object, it is a further object to have said single instrument selectively supply substantially pure white light to view dental targets, intensify said white light at a higher color temperature a limited amount for shade matching purposes simply by varying the voltage to the lamp filament by adjusting a potentiometer, supply non-polymerizing light illumination for viewing dental materials which otherwise would light polymerize light-sensitive materials, and supplying polymerizing light capable of quickly polymerizing light-polymerizable resins and plastics when required, whereby simple rotation of the aforementioned turntable on which said several light-modifying optical devices are supported in spaced relationship produces the desired types of dental illumination and photocure function from a single light source.

Another object of the invention is to provide a heat-absorbing filter positioned adjacent and in the path of the light beam emanating from a collimated light source, whereby the light beam is intercepted by the heat absorbing filter and produces relatively cool light, of reduced infrared wavelengths, and less thermal stress is placed upon the modifying optical filters when positioned in the light beam and in front of the reflector of the lamp.

A further object of the invention is to provide as a light source a tungsten halogen lamp having a parabolic reflector to produce substantially parallel light rays, and further to provide one or more light filters selectively positionable in the light path from the lamp and the reflector therefor. Beam-splitting flat mirrors also are positioned in the standard illumination beam and the no-cure beam which split the light beam into two separate light beams transmitted through said optical filters and reflect the same in separate directions respectively to spherical reflectors positioned at opposite sides of said lamp. Since each of the split beams are spaced apart, they reflect each of the beams forward, toward and through a fixed transparent window spaced forward from said lamp. Each of the separate light beams reflected from said spherical reflectors cross each other at a specified distance from said reflectors and are blended with the other beams to provide an illumination area of limited width and height at a location spaced forward from said window. The crossover of said light beams is at a range of distances at which a dentist normally positions an illuminating light source from a dental target such as an oral cavity. One reason for dual converging light beams is that, when a dentist is manipulating, it is possible to block one light beam with an arm, shoulder, hand, or head, whereby one light beam is left unblocked for illumination purposes.

Still another object of the invention is to provide a base movably mounted relative to a dental chair in an operatory for desired positioning of said base relative to a patient in said chair, and said aforementioned turntable upon which said aforementioned beam-modifying optical filters are mounted and is rotatably supported upon said base for movement around an axis vertical to said base, and further providing releasable position-maintaining means between said turntable and base to firmly hold a selected beam-modifying optical filter and associated beam-splitting flat reflectors in operable position adjacent said aforementioned lamp.

A further object ancillary to the immediate foregoing object is to mount said lamp fixedly and centrally adjacent one side edge of the base, which preferably is a plate, and also fixedly position said aforementioned spherical reflectors adjacent said same side edge of said base plate and spaced from opposite sides of said lamp, and said aforementioned transparent window is fixed to the opposite side edge of said base plate.

Still another object of the invention is to utilize optical filters and related mechanisms to change illumination emanating from a light source such as, for example, a tungsten halogen lamp, which filter system produces various desired Kelvin ranges respectively arranged to produce: (1) white illumination with a color temperature between 4700° K. and 5100° K. for normal observation of dental targets; (2) for color matching purposes, intensify the blue, green, and red toward the blue and thereby increase the lumens for shade matching by raising the color temperature to about 5500° K. or in a range between 5400° K. and 5900° K.; (3) for placing light cured dental restorations, without initiating curing, reduce the color temperature to less than 1667° K. and use the same with a filter which eliminates the blue range of the spectrum between 400 and 500 nm, and permits wavelength greater than 500 nm to pass through the optical filter, which renders polymerizing of visible light-polymerizable resins and plastics unaffected by the light; and a light beam having sufficient energy to polymerize actinic light activated materials. °K. arranged to be delivered to a light condensing means to polymerize actinic light activated materials.

It is another object of the invention to provide a multi-function, or multi-mode light apparatus for delivering light in selectable different modes derived from a collimated light source, at least one of the modes including a beam or beams of light and another mode including light delivered through a light pipe, with condensing means for condensing light from the source into the light pipe.

Details of the foregoing objects and of the invention as well as other objects thereof, are set forth in the following specfication and illustrated in the accompanying drawings comprising a part thereof.

BRIEF DESCRIPTION OF THE DRAWINGS

FIG. 1 is a side elevation of a dental operating light embodying the principles of the present invention and shown mounted on a fragmentally illustrated supporting arm.

FIG. 2 is a front elevation of the light shown in FIG. 1.

FIGS. 7A, 7B, and 7C are plan views of another embodiment which incorporates an optical condenser and a light pipe.

FIG. 8 is a section taken along lines 8—8 of FIG. 7A.

DETAILED DESCRIPTION OF THE PREFERRED EMBODIMENTS OF THE INVENTION

Figure 3:
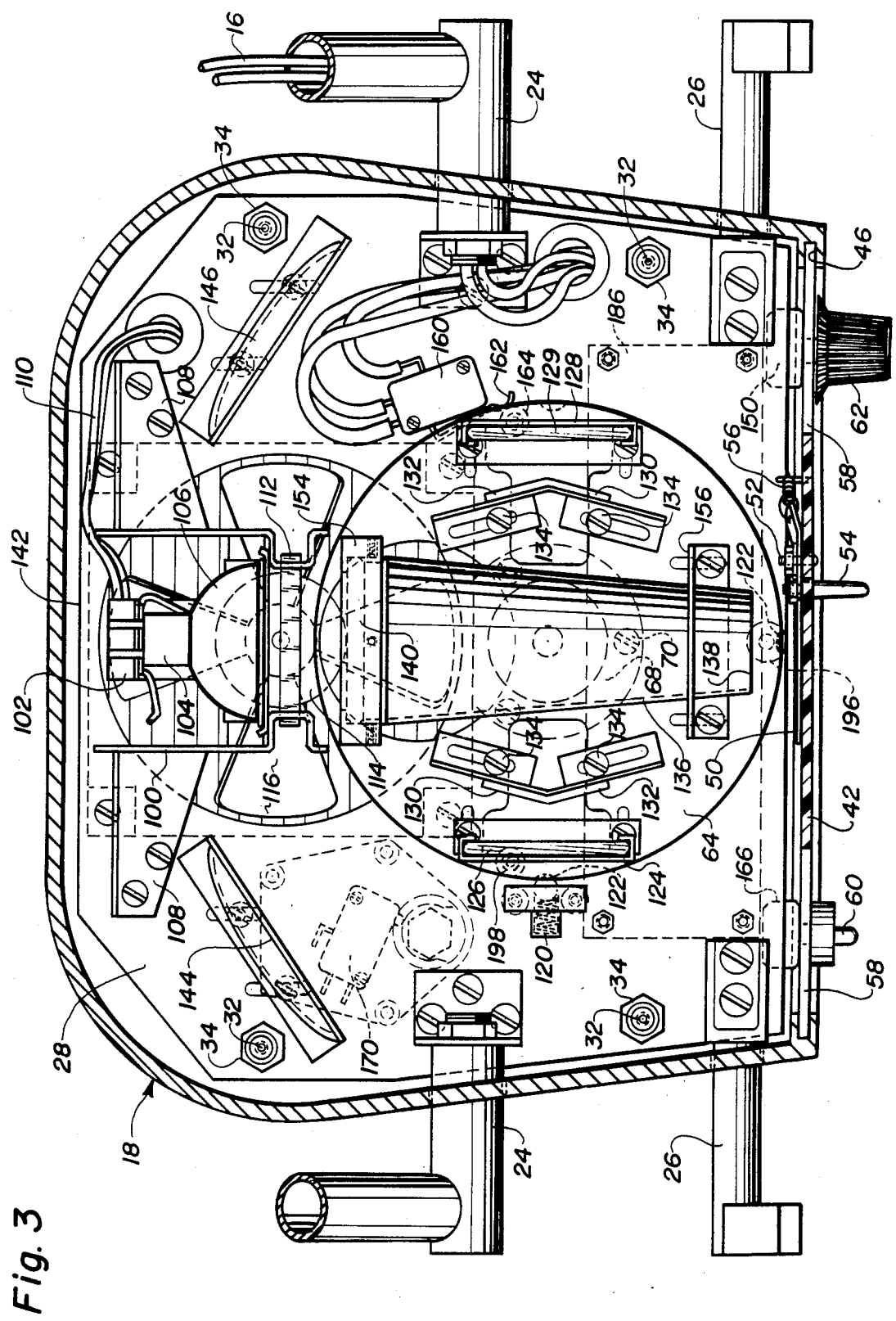
FIG. 3 is a horizontal sectional view of the light shown in FIGS. 1 and 2 taken on the line 3—3 of FIG. 2, said view being on a larger scale than the views in FIGS. 1 and 2.

It is believed desirable to set forth herein certain definitions and criteria pertinent to the present invention as follows:

Photometric power is that which the eye sees expressed in lumens/square meter or lumens/square foot.

Radiometric power is actual power from a given source expressed in watts/cm$^2$.

Nanometer (nm) is a unit of length of one cycle equal to one billionth of a meter or $10^{-9}$ meters.

Lumen (Lm) is a unit of luminous flux.

Footcandle (fc) is a unit of illuminance equal to one lumen per square foot.

Lux (Lx) is a unit of illuminance equal to one lumen per square meter.

Kelvin (K) is a unit of temperature equal in magnitude to 1° C. but based on an absolute temperature scale in which 0° K.$=-273.15°$ C.

Wavelength is the distance between two successive points of a periodic wave in the direction of propogation of a beam of light.

Hue is the attribute of a light source or object that determines whether it is perceived as red, orange, yellow, green, blue, or violet, without regard to the other aspects such as saturation and brightness.

In accordance with the present invention, the light source preferably is generated by electric current connected to a tungsten halogen lamp having a parabolic reflector, but other lamp types may be used such as various arc-type lamps which produce an acceptable optical spectrum. One particular selected tungsten halogen lamp found to be highly successful can be operated as high as 3400° K., but this is only exemplary and not restrictive. With this as a benchmark, however, for purposes of illustrating at least one example of the invention, the various lights or illuminations designed to be produced by such lamp require the use of specific optical filters to achieve the objectives of the invention for different dental illuminations and for photocuring purposes. In order to effect relatively cool light beam operation of the multi-function illuminating system of the invention, a heat absorbing filter preferably is positioned immediately in front of the lamp relfector in the light beam. With this exception, all of the other optical filters are interference filters which either pass or reject certain wavelengths of light, as designed and desired. These optical filters comprise layers of certain materials selected for their known index of refraction and are laminated, for example, in a vacuum deposition chamber, and laid on a suitable substrate. Such optical filters shape the spectrum of a light beam pssing therethrough to a desired portion or section of the optical spectrum for specific passage or rejection of light beams of various wavelengths.

Light beams also have color temperature units expressed as K or Kelvins. According to one specific set of examples of ranges of color temperatures, but without limitation thereto, relative to the present invention, the optical filter to produce substantially pure white light for normal illumination of dental targets from the reflector of the lamp referred to produces beams having a color temperature between 4700° K. and 5100° K. in the wavelength range between 400 and 715 nm and in which the blue, green, and red wavelength ranges are proportioned to produce pure white light.

For shade matching of artificial teeth with natural teeth, this temperature is increased to approximately 5500° K. but with an adjustable range from 5400° K. to 5900° K. which is accomplished by increasing the voltage beyond the standard illumination range supplied to the filament of the lamp.

For observation of a dental target which requires illumination and, therefore, exposure of light-curable resins or plastics to certain beams without activating the material, a filter to produce a beam having a color temperture of less than 1667° K. is used but the filter is one which eliminates the 400 to 500 nm wavelength range, yet retains light beams between the 500 and 715 nm wavelength range which is necessary for viewing purposes and allows placing and shaping the observed light-sensitive material such as visible light-curable filling or denture base resins or plastics. Such beams are in the yellow-red region of the spectrum.

For curing light-sensitive resins and plastics, the invention includes a photocure heat reflecting band pass filter positionable opposite the parabolic reflector of the lamp, which heat absorbing filter which has a color temperature of less than 1667° K. with its light flux primarily in the 400 to 500 nm wavelength range and which rejects beams in the wavelength range betwewen 500 and 715 nm. A light-condensing means, either optical or in the form of a cone, is used when photocuring is required.

In producing the above-described types of illumination and for photocuring purposes, another objective of the invention preferably is to project beams from the apparatus in a collimated form and of reasonable dimensions in an area at a conventional distance of approximately in the range of between 24 and 37 inches between the dental target and the light source. In an alternate embodiment, the light is condensed and directed into a flexible light tube, for delivery of a high intensity light to a relatively small target area.

As an improvement ancillary to the foregoing object, the circuit to the lamp also includes an additional, preferably push-button, switch which is actuated easily to restore current to the lamp after the external supplmental cone has been mounted operatively upon the internal primary cone and, still further, a timer of limited time duration also is in the lamp circuit and functions to disconnect current from the lamp after a pre-set time elapses, such as ten seconds duration, for example, thereby automatically limiting exposure by the photocure light beam. The above described push-button switch may be actuated repeatedly, however, to afford as much photocuring as required.

Having set forth above exemplary parameters of physical aspects of the illuminating apparatus of the present invention, it is to be understood that the criteria described may be changed within reasonable limits without departing from the spirit of the invention. Specific illustrations of physical apparatus which utilize said criteria are set forth below.

The Apparatus

Referring to FIGS. 1 and 3 of the drawings, it is intended that the multi-function dental operating light source comprising the present invention by supported by the outer end of an appropriate arm 10 which extends either from a wall, ceiling, or post pedestal in an operatory. A U-shape member 12 is connected by a swivel 14 to the outer end of arm 10 and it will be understood that an electrical supply cord is located in conduit 16 and extends from a suitable power line source, not shown, and appropriate electrical thermal breakers, current-limiting switch, and connect-disconnect switch and its wiring are located in said conduit which extends in conventional manner through the arm 10, swivel 14, and U-shape member 12 to the interior of the light head housing 18 which preferably comprises an upper section 20 and a lower section 22 that are detachably connected. Opposite sides of the housing 18 are connected by pivots 24 to the outer ends of member 12.

The sections 20 and 22 of housing 18 preferably are molded from suitable, rigid plastic material for durability as well as to provide electrical insulation properties. Further, a manually-engageable handle 26 extends from each of the opposite sides of the housing 18 for purposes of swivelling the housing to any desired location and position for purposes of directing illumination or photocuring light beams therefrom to a dental target such as an oral cavity or tooth of a patient. It will be understood that the pivots 24 and swivel 14 have sufficient friction to maintain a desirable location and position of the housing 18 after the same has been adjusted to a working position.

Referring particularly to FIG. 3, a description of the contents of the housing 18 is as follows. In said figure, it will be seen that there is a base 28 which preferably is a plate substantially parallel to the meeting lines of sections 20 and 22 of the housing, said base plate preferably being of metal, such as aluminum, and may be anodized black or in color. Elements 32 comprise the upper portions of posts which extend perpendicularly from base 28 and extend through suitable holes in the base plate. The lower part of the upper portions 32 are threaded to receive clamping nuts 34 and accomplish this without threading the entire portions 32 by the part thereof which receives the nuts 34 being of a slightly larger diameter than the upper part of said portions. The outer ends of upper portions 32 have tapped holes, not shown, for purposes of receiving connecting screws 38 which extend through bases 40 shown in FIG. 1 on the interior of the upper and lower sections 20 and 22 of the housing 18. FIG. 3 reveals the upper portions 32 of four composite posts (not shown) respectively adjacent the corners of base 28. These composite posts comprise the means for holding together the upper and lower sections 20 and 22 of the housing 18.

The front wall of the housing 18 has a transparent window panel 42 which, in vertical elevation, is shown in FIG. 2 in the forward portion of the housing 18 and has a bezel 44 surrounding the same. Said bezel has a continuous groove 46 extending thereinto as best seen in FIGS. 2 and 3 and said groove receives the edge portions of the transparent window panel 42 for purposes of securing it in operative position. The panel has a small opening or apertue 48 near the upper portion and midway between the opposite sides through which the photocuring light can pass when the same is open, details of which are described hereinafter. The opening 48, however, normally is closed except when the external light-condensing cone is mounted upon the primary internal cone, whereby its effects are employed to activate light-curable resins and the like when aligned with said opening. Closing of opening 48 is effected by a closure in the form of a pivoted plate 50 which is shown in edge view of FIG. 3 in the lower portion of said figure. The closure 50 is supported upon a pivot bolt 52. To manipulate the closure, a pin 54 which is attached thereto projects through the opening 48 as clearly shown in FIG. 2. It is otherwise shown in FIG. 3, where it will be seen that it is adequate for manual engagement. Closure 50 normally is maintained in closed position in a yieldable manner by means of return spring 56. The window panel 42, in each of the opposite upper corners thereof, is provided with clear transparent window portions 58 and, otherwise, the window panel 42 is opaqued, such as by painting the inner surface thereof or otherwise. The lower opposite corners of the window panel 42 also are provided respectively with holes through which a push-button actuator 60 and a shaft of a potentiometer extend.

Base plate 28 supports a number of elements within housing 18, among the more important of which is a turntable 64 which is shown in plan view in FIG. 3. Said base is provided with a preferably circular opening 66 into which a shouldered, preferably circular insulating insert member 68 is suitably affixed by spaced screws 70, certain of which are shown in FIG. 3. Rotatable shaft 72 extends through a central opening in insulating member 68.

Shaft 72 has a depending portion which extends through the lower section 22 of housing 18 as shown in FIG. 1 and to the projecting end thereof, a manually-engageable, rotatable knob 98 is affixed. The foregoing arrangement is for purposes of positioning the plurality of different beam-developing devices circumferentially mounted upon the turntable 64 relative to a light source, details of which are described hereinafter.

Base 28 is fixedly mounted within the housing 18 by means of the details not shown. Also supported fixedly upon said base plate is a lamp housing 100 provided with an insulating base insert 102 which receives and supports base plate 104 of a preferably tungsten halogen lamp 106 which has a parabolic reflector for purposes of producing a collimated light beam. The housing 100 has a pair of ears 108 which are secured by screws to the base 28 as clearly shown in FIG. 3. Connected to insulating base insert 102 are a pair of electric wires 110 which are part of the electric cord 16.

The forward portion of the lamp housing 100 has an opening through which the collimated light beams from the parabolic reflector of lamp 106 are projected and extending across that opening is a heat absorbing filter 112. Further for purposes of rendering operation of the multi-function light source within a dental operatory relatively cool, supported adjacent an opening in the fixed base plate 28 and upon the lower surface thereof is a forced air cooling fan unit 114, shown in phantom in FIGS. 1 and 2 and in plan view in FIG. 3, said unit including a bladed fan 160 which blows ambient room air directly through the housing 100 and in doing so draws air in through louvre 118 in the lower section 22 of the housing and discharges it through louvre 118 in the upper section 20 of the housing 18.

The Turntable

As described hereinabove in a general manner in the objects of the invention, one of the highly important features of the present invention comprises the turntable 64, the mounting of which is described hereinabove, and of the light beam-modifying elements which are supported thereon for rotation therewith to dispose the same respectively in one of three operative positions relative to the fixed light source 106 which preferably is a tungsten halogen lamp but other lamps of suitable and similar capability to produce a suitable optical spectrum may be substituted therefore, if desired. By actual experience, however, it has been found that said specific type of lamp performs admirably for all of the purposes to which the present invention is directed. Also as indicated above, there are three principal types of light beams capable of being produced by the invention by means of certain individual filters respectively producing (1) pure white illumination meaning the absence of color hue, (2) no-cure illumination, and (3) photocuring power.

With reference to FIG. 3, it will be seen that the base 28 supports a spring-actuated positioning unit 120 which releasably engages complimentary shallow recesses 122 in the periphery of the turntable 64 to accurately position the various beam-modifying optical elements. The first beam-modifying optical element or system comprises a perpendicular frame 124 which supports a perpendicular filter 126 adapted to develop from lamp 106 and adjacent reflectors a standard illuminating beam which is pure white and devoid of color hue. Opposite the frame 124 is a similar perpendicular frame 128 which supports a no-cure filter 129. The light beams from filters 126 and 129, when they individually are disposed adjacent the lamp 106 and in axial alignment thereof respectively are divided by angularly positioned reflecting flat mirrors or light beam-dividers 130 and 132 which are secured by means of a bracket through which screws 134 project for securing the brackets to the turntable 64. One set of such reflecting mirrors 130 and 132 are provided respectively for each of the filters 126 and 129.

Mounted between the sets of reflecting mirrors or members 130 and 132 is a diametrically extending light reflecting device comprising a frustro-conical light-condensing cone member 136. The light output end 138 of member 136 is smaller than the operative light input end which is shown in FIG. 3 to be adjacent the lamp 106 for purposes of receiving collimated light rays from the parabolic reflector of lamp 106. The light rays also pass through a heat reflecting and band pass filter 140 for purposes of reshaping the optical spectrum of the light-curing beam.

Standard Illumination Beam

Figure 4:
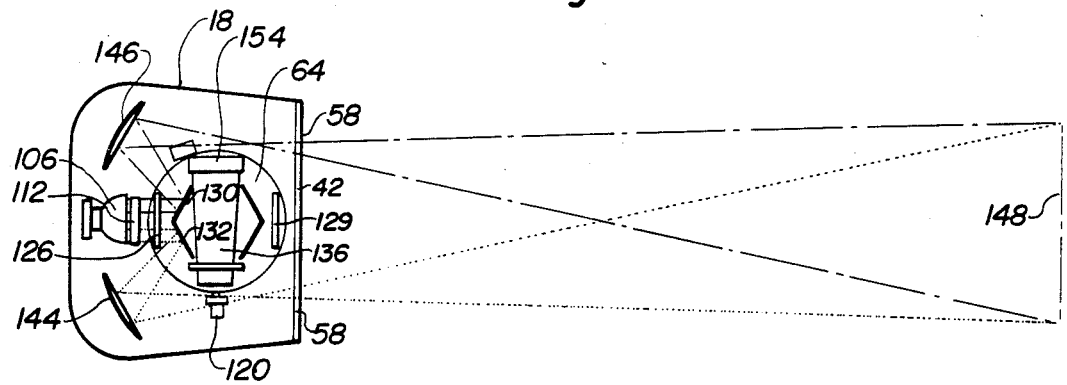
FIGS. 4 to 6 respectively are partially diagrammatic plan views respectively of the three principle operative positions in which the light functions to produce a variety of illuminations for dental use.

Referring to FIG. 4, it will be seen that the filter 126 is disposed adjacent the heat absorbing filter 112 and in immediate alignment with the parabolic reflector of tungsten halogen lamp 106. Adjacent the rear edge of the base, somewhat at the corners thereof, are a pair of spherical reflectors 144 and 146 which are shown better in FIG. 3. These have been adjusted to receive light from the divided beams from the flat mirrors 130 and 132 which, in turn, reflect the light forward through the clear transparent window portions 58 of the front panel 42. Light rays reflected from the spherical reflectors 144 and 146 will travel nearly parallel to each other and spaced apart as shown in FIG. 4 while others will cross each other at defined distances as also shown in said figure, the result being that a column of light beams for standard illumination, comprising pure white light, are developed over a reasonable area 148 which, at a distance of about between 24 and 37 inches from a dental target will be in the range of approximately 4 inches high and 8 inches wide, such description primarily being exemplary rather than restrictive.

The beams produced will be of a pure white nature, free of color hue due to the nature of a filter 126. Further by way of a specific example, assume that the color temperature of the lamp 106 is approximately 3000° K. The filter 126 produces a color temperature within the range of 4700° K. and 5100° K., the wave length range being between 400 nm and 715 nm. The same type of white light also is preferable for shade matching of artificial teeth relative to natural teeth or any other objects requiring color comparison but preferably such light must be of a higher color temperature such as of the order of 5000° K. This is produced also by optical filter 126 but the voltage to lamp 106 is increased by manipulating the knob 62 connected to potentiometer 150, as seen in FIG. 3. Knob 62 and potentiometer 150 suitably provide a plurality of positions for setting the voltage applied to lamp 106, and thus its corresponding lamp temperature. This combination is also used to provide discrete voltages to the lamp for the embodiments of FIGS. 7A, 7B, and 7C discussed below.

No-Cure Illumination

Figure 5:
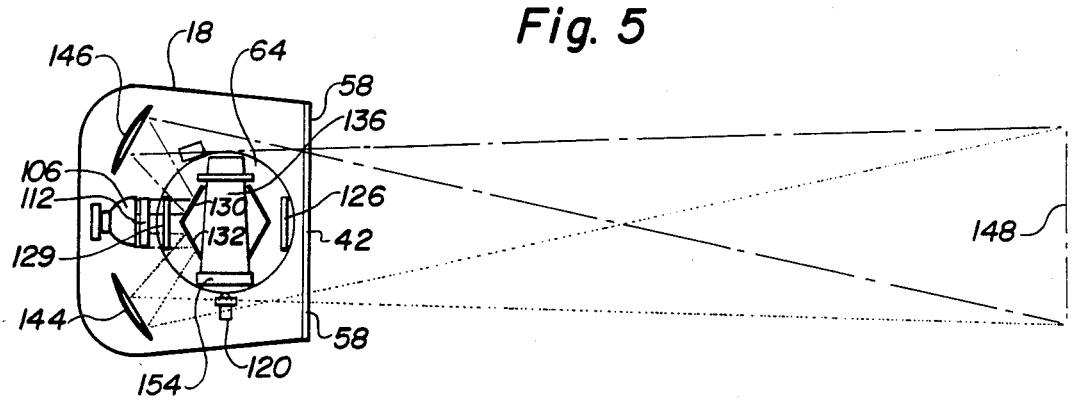

Referring to FIG. 5, this illustration pertains to the no-cure illumination light beam and to produce this, the turntable 64 is rotated to position optical filter 129 opposite the lamp 106, where it will be held by means of one of the depressions 122 in the turntable engaging the spring-pressed ball detent of the positioning unit 120. Optical filter 129 is different from optical filter 126 in that it is designed to reject beams having wavelengths between 400 and 500 nm and therefore are not present in the light beam produced of the lamp whereby the resulting non-curing light beams are in the blue region of the visible spectrum and are incapable of ploymerizing light-polymerizable plastic. However, the optical filter also is capable of passing the light beams between 500 and 715 nm for purposes of viewing light-curable material, without activating it, such as when the same is being placed, contoured, and characterized in a tooth or teeth. The passage of light beams between 500 and 715 nm is suitable for such illumination and viewing purposes and is in the yellow-red region of the visible spectrum.

As is in regard to the description relative to FIG. 4, the light beams produced by the parabolic reflector of lamp 106 and filter 129 are reflected by the spherical reflectors 144 and 146 to project foward both the parallel light beams and those which cross at defined distances and ultimately result in producing an illuminating area 148 within the ranges stated with respect to optical filter 126 in FIG. 4.

Photocuring Light Power

Figure 6:
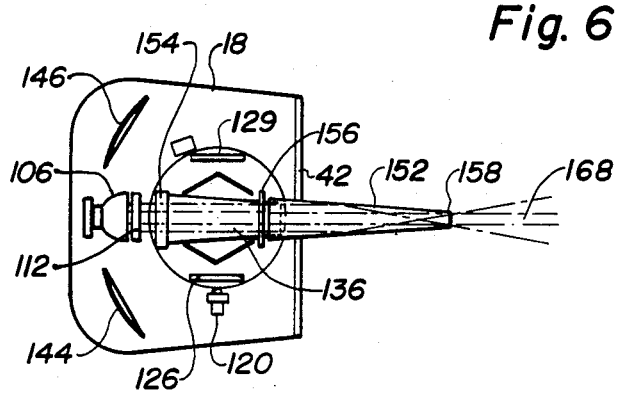

When the photocuring function is to be produced by the invention, the turntable 64 is rotated to the position shown in FIGS. 3 and 6 in which the internal primary condensing cone member 136 is disposed with the larger light input end adjacent the lamp 106 and the outer smaller light output end 138 thereof immediately adjacent the opening 48 in the window panel 42. The light-condensing primary cone member 136 may have a supplemental externally mounted light-condensing cone member 152 (FIG. 6) attached to its output end 138 by friction or otherwise, to effectively extend its length. Support 154 is fixed at its lower end to turntable 64 and, in addition to supporting the heat reflecting and band pass filter 140, also supports the larger inner end of the primary light-condensing cone member 136, while the smaller end 138 thereof is supported by a bracket 156 and is attached by screws to turntable 164 as clearly shown in the lower portion of FIG. 3.

Preferably, the interior of light-condensing cone member 136 has a highly specular light-reflective surface which, for convenience, for example, may comprise a highly polished electrobrightened aluminum interior liner, and similarly, such liner lines the inner wall of the supplemental external light-condensing cone member 152 which, when rendered operative, is extended through the small opening 48 in the window panel 42 and then is mounted upon the small end 138 of internal light-condensing cone member 136. A substantial amount of collimation of light rays from the reflector of lamp 106 occurs when mounted as shown by phantom lines illustrated in FIG. 6 by the beams delivered from the discharge end of supplemental external light-condensing cone member 152 which diverge only to a limited extent of about 10° from the optical axis in order to provide greater penetration of a light-curing beam into light-polymerizable or photocurable plastic material. A low light ray divergence angle is desirable for purposes of activating the same and thereby produce a rigid dental restoration having a greater depth of cure. In normal operation, the tip or outer end 158 is disposed relatively close to the dental target which is to be activated by the light energy emanating therefrom.

When a turntable is disposed in the position shown in FIGS. 3 and 6, wherein the member 136 is in active position for receiving beams from the lamp 106 and assuming that the member 136 is directed toward a patient's face such, for example, as when it is positioned for purposes of having the supplemental member 152 affixed thereto, the intense light emanating from the internal primary light-condensing cone member 136 is very bright and would present a safety problem as well as being very annoying to a patient if directed thereto. To prevent this from occurring, the invention contemplates the use of a disconnecting switch 160, which has an actuating finger 162 engaged by a camming roller 164 which is shown adjacent the finger 162 in FIG. 3. It will be seen that when the turntable 64 is rotated, for example, from either of the positions shown in FIGS. 4 and 5, to the position shown in FIG. 6, the finger 162 will be engaged by the roller 164 and open the switch and thereby disconnect the lamp 106 from the supply circuit so that it will not shine through the open end 138 of member 136.

After the supplemental external light-condensing cone member 152 has been attached over the outer end of member 136, as shown in FIG. 6, an additional switch 166, as seen in FIG. 3 in the lower left-hand corner, is actuated by push-button 60 to re-establish the current to the lamp 106 for the purpose of creating light beam 168 which is of a light-curing nature and emanates from the light output end 158 of the external light-condensing cone member 152.

Figure 7A:
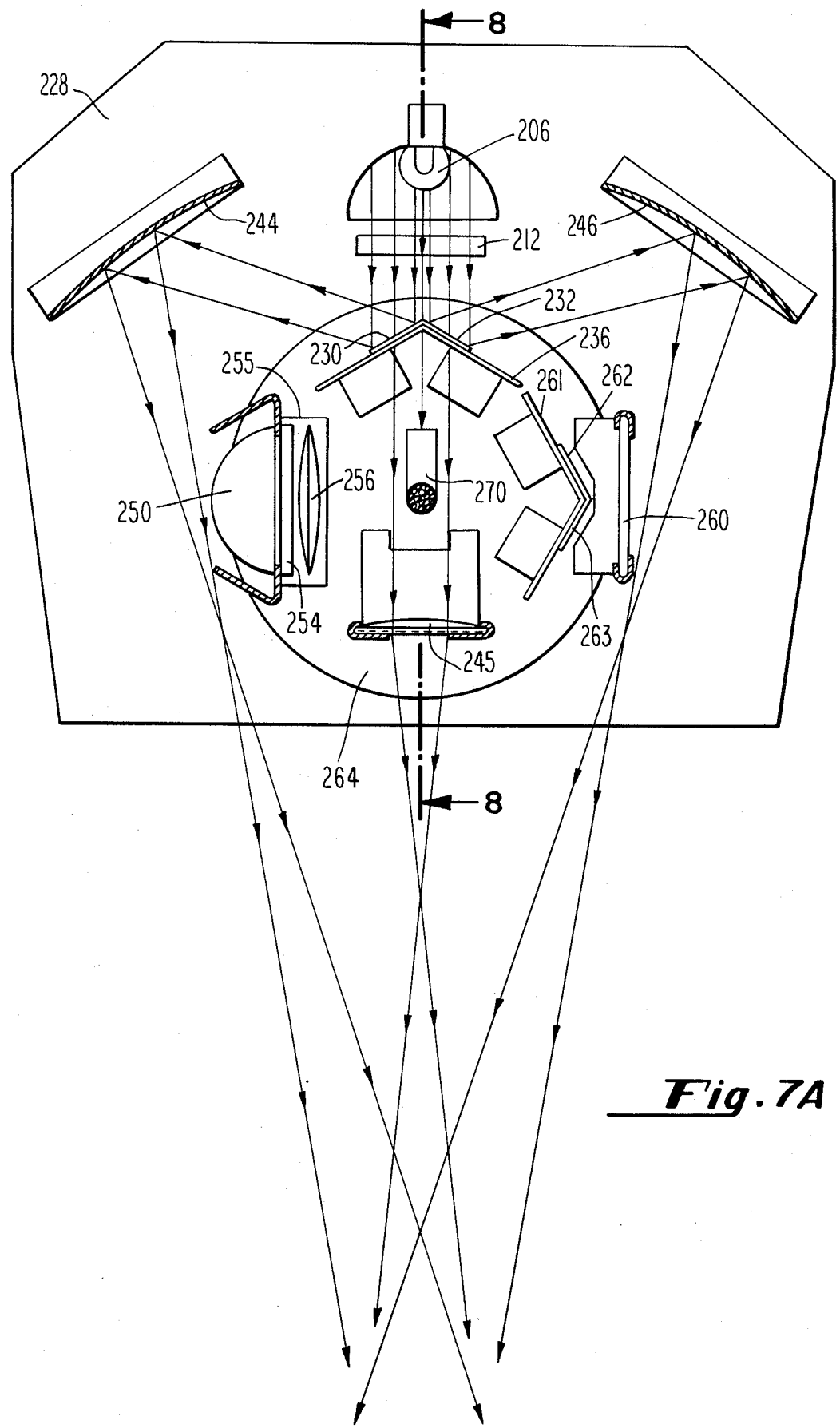
Figure 7C:
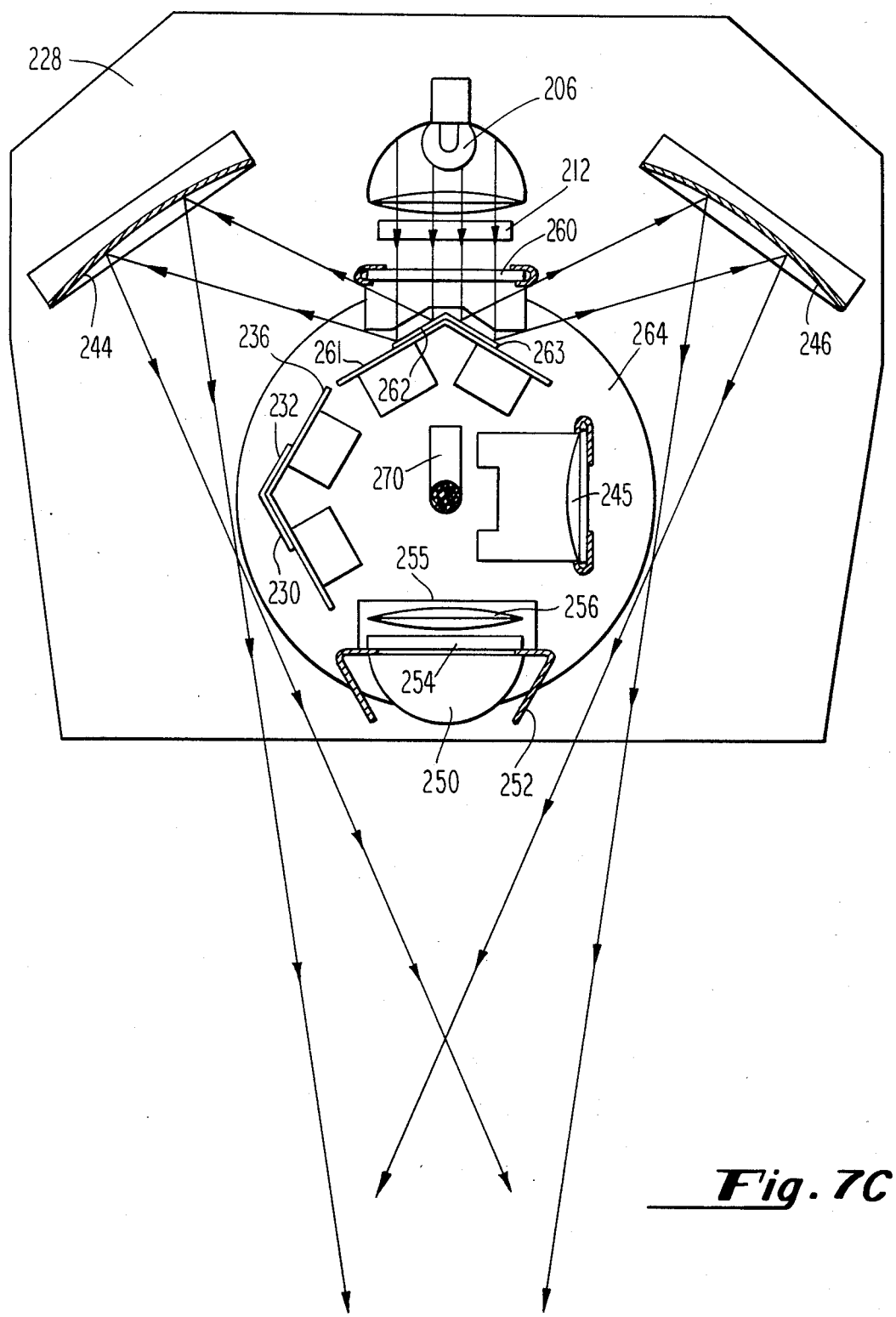

Referring now to FIGS. 7A, 7B, and 7C there are shown plan views of an alternate embodiment, wherein a different turntable arrangement is utilized for providing a different combination of selectable light modes, i.e., forms of light delivery. The turntable is rotatable in a manner as set forth above, to provide different combinations of light outputs in accordance with the elements that are brought into the path of the light source at the respective turntable positions.

FIG. 7A shows the turntable in a position to generate three light beams for general illumination, plus a light pipe output for transillumination of small target areas. In this arrangement, the potentiometer 150 (FIG. 3) is set by the operator to provide a voltage setting of, e.g., 32, 35, or 38 volts, corresponding to a bulb temperature of about 2864° K., 3009° K., or 3075° K. respectively. A pair of reflector mirrors 230, 232 mounted on a support 236 are positioned to reflect light from collimated source 206 toward and off of spherical reflectors 244, 246, to provide two converging beams. In addition, support 236 contains a slot, or window 237 positioned just below reflectors 230, 232, as further illustrated in FIG. 8. This slot permits a portion of the light from source 206 to pass directly through above the center of the turntable. Much of the beam passes through to focusing lens 245, which is held in position by support 247 having a window 248. The lens and window are positioned to direct the center beam of light so that it substantially meets with the two converging side beams at a predetermined distance. Also shown in FIG. 7A is the input end 270 of a light pipe 278, having an input tip 271 positioned to collect slightly off axis light from the center beam. The lamp 106 produces substantially collimated light, but some light diverges off axis, and tip 271 is positioned slightly off the axis of the center beam. As seen in FIG. 8, the light pipe is connected mechanically to cover 274 through ring or collar 275, the main portion of light pipe 278 being flexible and of a sufficient length to enable the dentist to direct the output end 280 at any desired target location. The input tip collects essentially off axis light from the center beam, while the bulk of the collimated portion of the beam passes on to and through window 248.

The light pipe 278 thus provides additional ability to capture the off axis light of the center beam, e.g., an operator can additionally direct the light pipe output to transilluminate tissues in the oral cavity, such as a tooth, or the light pipe may be used for high intensity spot illumination, such as in the posterior areas of the oral cavity.

Referring now to FIG. 7B, the turntable 264 is shown rotated into another position so as to provide only a photocure light for light curing procedures. For this application, the lamp is preferably operated at 47 volts, corresponding to a lamp temperature of about 3254° K. The collimated light from source 206 is condensed and direced into the tip portion 270 of light pipe 278, providing intensified light for purposes of light curing of a restoration. A condensing means particularly adapted for this application comprises a spheric lens 250 and biconvex lens 256. This combination provides a very short focal length condensing means of the collimated light, e.g., 1 cm distance, and directs it into the tip 271 of the receiving portion 270 of the light pipe. A band pass filter passing visible light in a range of about 400-500 nm is mounted between spheric lens 250 and the biconvex lens 256. Further, a shield 252 prevents scattering of light from the spheric lens toward either reflector 244 or 246, ensuring that no light is directed toward the patient from those reflectors. Any straight ahead light is blocked by the back side of mirror support 261. Thus, the high intensity cure light is available through the light pipe, while at the same time the patient is shielded from any other light beam being directed on his or her face. As illustrated in FIG. 8, the light pipe 278 is flexible, and can be manipulated by the operator to direct the output end 280 at any desired target, e.g., a photocurable restorative that has been placed in a patient's tooth.

Referring now to FIG. 7C, there is shown a third position of turntable 264, providing for two converging beams reflected from reflectors 244, 246, the beams being filtered additionally by color correction filter 260 for shade matching purposes. Filter 260 is illustrated in a position directly in front of source 206, and is designed to modify the source light spectrum from the parabolic reflector such that the visible light power distribution in the beams delivered to the target meet the color rendering index greater than 90 required for shade matching of teeth, particularly for matching of new artificial teeth to natural or tooth surfaces, as described above in connection with the embodiment of FIG. 4. Mirrors 262, 263 are also rotated into position, to reflect light off of reflectors 244 and 246, thereby generating two converging beams for the shade match application. Since there is no window in support 261, there is no straight-ahead beam, and there is no light that gets through to the light pipe tip 270. For this application, the lamp is operated at a voltage of about 41 volts, corresponding to a lamp temperature of about 3175° K.

I claim:

1. Light apparatus, having a light source generating light directed substantially along an axis, including:
    delivery means mounted for movement relative to said light source and having a plurality of operative positions selectable for delivering light to a given target by a selected one of a plurality of delivery modes due to said movement, including beam means for deriving at least one beam mode of light from said source and delivering said beam of light to said given target, and light pipe means for collecting light from said source and delivering said collected light to said given target, and
    selecting means for operatively selecting the mode of operation of said delivery means so as to cause it to deliver at least one of said modes of light.

2. The light apparatus as described in claim 1, further comprising filter means operatively selectable for filtering selected ranges of wavelengths from the light generated by said source, and
    said selecting means further comprising means for selecting the range of wavelengths at which said filter means operates.

3. The light apparatus as described in claim 1, wherein said light apparatus is dental operative apparatus, and further comprising selectable filter means for filtering the light generated by said source to provide shade matching.

4. The light apparatus as described in claim 1, wherein said apparatus is dental operative apparatus, in comprising a visible band pass filter operative in association with said light pipe means, for delivering curing light through said light pipe means.

5. The light apparatus as described in claim 1, comprising selectable axial beam means for delivering a beam of light directed substantially along said axis, and pipe positioning means operatively selectable with said axial beam means for collecting light from the beam passing through said axial beam means.

6. The light apparatus as described in claim 1, wherein said beam means further comprises means for generating plural light beams, and said selecting means comprises means for selecting respective combinations of said beams to be directed at said target.

7. The light apparatus as described in claim 6, wherein said beam means comprises means for directing a center beam substantially along said source axis, and for directing at least one other beam at an angle from said axis and converging with said axis at a point a predetermined distance in front of said source.

8. The light apparatus as described in claim 1, wherein said light pipe means comprises condensing means for condensing light along the path of said axis, and a light pipe having its input positioned to collect said condensed light.

9. The light apparatus as described in claim 8, comprising a bandpass filter positioned between said light source and said condensing means, and wherein said condensing means comprises an aspheric lens and a biconvex lens.

10. The light apparatus as described in claim 8, wherein said condensing means has a focal length of about 1 cm.

11. Light apparatus, having a single light source which generates substantially collimated light directed along an axis, and comprising
  beam means operatively selectable for generating from said source plural respective beams of light, including at least one beam directed at an angle from said axis and converging with said axis at a point a predetermined distance in front of said source, and a center beam directed substantially along said axis,
  filter means operatively selectable for filtering selected ranges of wavelengths from the light generated by said source,
  condensing means operatively selectable for condensing said center beam of light along the path of said axis,
  light pipe means for collecting said condensed light and delivering it to a desired location, and
  selecting means for operatively selecting a desired combination of said light beams, wavelength ranges and condensing means.

12. Dental operative light apparatus having a single light source which generates substantially collimated light directed along an axis, including
  optical condensing means having a plurality of operative positions for condensing light along said axis,
  light pipe means for collecting said condensed light and transmitting same to a chosen location,
  selectable positioning means for positioning said optical condensing means in one of said plurality of positions, one of said positions enabling it to condense light along said axis, and
  beam means having a plurality of operative beam positions for generating from said source plural beams of light including at least one beam at an angle from said axis and another beam along said axis, and said positioning means further having means for positioning said beam means to one of said beam positions.

13. The dental operative light apparatus as described in claim 12, further comprising filter means operatively positioned by said positioning means for filtering of selected ranges of wavelengths from said light.

14. A method of applying a selected form of light to a dental target, comprising
  generating from a single light source a light directed substantially along an axis,
  selecting from selecting means having a plurality of operative positions for an output form of said light, said operative positions comprising (a) a plurality of beams directed at different angles, (b) a concentrated light from a light pipe and (c) at least one beam and a concentrated light from a light pipe, and
  delivering light to the dental target in the form of a the selected light output.

15. The method of claim 14, further comprising selecting a desired wavelength content and filtering the selected form of light in accordance with said selected wavelength content.

16. The light apparatus as described in claim 15, having a voltage control means which is adjustable to operate said light source at a light temperature within a range of about 3000° K. to 3200° K. for general illumination purposes.

17. Light apparatus, having a light source generating light directed substantially along an axis, including:
  delivery means operatively selectable for delivering light to a given target by a selected one of a plurality of delivery modes, including beam means for deriving at least one beam of light from said source, and light pipe means for collecting light from said source and delivering said light to said given target, said delivery means having a combination mode for delivering at least one selected light beam and concurrently delivering light from said light pipe means, and
  selecting means for operatively selecting the mode of operation of said delivery means so as to cause it to deliver at least one of said modes of light.

* * * * *